(12) United States Patent
Ward et al.

(10) Patent No.: US 6,360,740 B1
(45) Date of Patent: Mar. 26, 2002

(54) METHOD AND APPARATUS FOR ASSISTED BREATHING

(75) Inventors: Leif Ward, Dalarö (SE); Siegfried Kallert, Erlangen (DE); Harald Kirchner, Fuerth (DE); Brigitte Stroetmann, Nuremberg (DE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/417,499

(22) Filed: Oct. 13, 1999

(30) Foreign Application Priority Data

Oct. 14, 1998 (SE) .............................................. 9803508

(51) Int. Cl.[7] ............................................. A61M 15/00
(52) U.S. Cl. ............................ 128/200.24; 128/202.13; 128/202.16; 607/42
(58) Field of Search ...................... 128/200.24, 202.13, 128/202.16; 607/2, 3, 20, 42

(56) References Cited

U.S. PATENT DOCUMENTS

| | | | | |
|---|---|---|---|---|
| 4,237,899 A | * | 12/1980 | Hagfors et al. ................ 607/46 |
| 4,326,513 A | * | 4/1982 | Schulz et al. .......... 128/203.14 |
| 4,506,666 A | * | 3/1985 | Durkan .................. 128/204.23 |
| 4,570,631 A | | 2/1986 | Durkan .................. 128/204.23 |
| 4,681,121 A | * | 7/1987 | Kobal .................... 128/203.14 |
| 4,830,008 A | * | 5/1989 | Meer .......................... 607/42 |
| 4,928,674 A | * | 5/1990 | Halperin et al. ........... 128/30.2 |
| 5,036,848 A | | 8/1991 | Hewson ......................... 607/2 |
| 5,146,918 A | * | 9/1992 | Kallok et al. ................... 607/2 |
| 5,584,290 A | | 12/1996 | Brain ..................... 128/207.15 |
| 5,678,535 A | * | 10/1997 | DiMarco ...................... 607/42 |
| 5,953,713 A | * | 9/1999 | Behbehani et al. ........... 706/16 |
| 6,116,241 A | * | 9/2000 | Huygen et al. ........ 128/203.14 |
| 6,149,670 A | * | 11/2000 | Worthen et al. ............... 607/3 |

FOREIGN PATENT DOCUMENTS

| | | |
|---|---|---|
| DE | PS 588 091 | 10/1933 |
| DE | AS 1 766 589 | 8/1971 |
| DE | 295 20 326 | 6/1997 |
| EP | 0 438 863 | 7/1991 |
| WO | WO 86/00234 | 1/1986 |
| WO | WO 97/38751 | 10/1997 |
| WO | WO 98/25664 | 6/1998 |

* cited by examiner

*Primary Examiner*—Aaron J. Lewis
(74) *Attorney, Agent, or Firm*—Schiff Hardin & Waite

(57) ABSTRACT

A system for assisted breathing has a ventilator delivers a breathing gas to a living creature in order to facilitate, support and/or control the breathing of the living creature. The respiratory musculature is weakened during treatment with a ventilator, long-term treatment in particular, and this results in longer treatment times, especially weaning times. Accordingly, a stimulation apparatus, devised for connection to the living creature, is incorporated into the system for assisted breathing in order to stimulate the respiratory nervous system and/or respiratory musculature of the living creature. Weakening of the respiratory musculature can be reduced by the stimulation apparatus emitting a stimulation signal at specific intervals.

17 Claims, 2 Drawing Sheets

METHOD AND APPARATUS FOR ASSISTED BREATHING

BACKGROUND OF THE INVENTION

1. Field of the Invention

The present invention relates to a method and a system for assisted breathing of the type having a ventilator which delivers breathing gas to a living patient.

2. Description of the Prior Art

A patient may need respiratory assistance as a result of disease and injuries of various kinds. The need can be direct, especially when the injury or illness afflicts the patient's respiratory system. The need can also be indirect, e.g. during anaesthesia and some intensive care. The respiratory assistance can encompass everything from facilitating spontaneous breathing to total control of breathing. A ventilator (respirator) is usually employed to provide the breathing assistance.

It should be noted that a "patient" in this context could be any living creature, i.e. human or animal.

One problem occurring in long-term controlled respiration is that the patient's own respiratory musculature becomes weakened. In many instances, the patient then loses the ability to breathe spontaneously after the true need for assisted respiration has been eliminated. Weaning the patient off the ventilator then takes longer. This cause a cost increase to the society in the form of longer treatment duration times and, more important, increases the discomfort and risk of secondary disease for the patient.

Another problem related to ordinary respiratory assistance is that the assistance itself does not precisely mimic normal respiration.

The normal mechanics of breathing are based on the active creation of a negative pressure in the lungs through the use of the respiratory muscles. Air is then sucked into the lungs during inhalation. Through this negative pressure in the lungs and thorax, an improved filling of the heart and increased heart output occur. Exhalation is passive and follows after relaxation of the respiratory muscles.

During respiratory assistance, however, gas is supplied to the patient at an elevated pressure. During inspiration, the pressure in the lungs is therefore higher during respiratory assistance than during normal inhalation. This increased pressure will influence the circulatory system. The increased pressure in the lungs and thorax will cause a lessening of the filling of the heart and a lower heart output. At very high positive pressures there is also the risk of barotrauma and overdistension.

One known way of trying to simulate normal breathing mechanics, is to stimulate either the nerves (in particular the phrenicus nerve) leading to the respiratory muscles (in particular the diaphragm) or the muscles themselves.

SUMMARY OF THE INVENTION

An object of the present invention is to provide a method and system for assisted breathing wherein weakening of respiratory musculature during respirator treatment with a ventilator is reduced or prevented.

Another object of the invention is to provide such a method and system for assisted breathing wherein weaning time after respirator treatment with a ventilator is shortened.

Another object is to provide such a method and system wherein substantially normal breathing mechanics can be provided by artificial respiratory assistance.

The above objects are achieved in accordance with the principles of the present invention in a method and an apparatus wherein a ventilator delivers breathing gas to a living subject in order to facilitate, support and/or control the breathing of the subject, and wherein the subject is also connected to a stimulation apparatus which stimulates an anatomical portion of the subject which participates in breathing, such as the respiratory nervous system and/or the respiratory musculature, and wherein the stimulation apparatus stimulates the subject at specified intervals.

Several advantages are achieved by the use of a stimulation apparatus, which directly or indirectly stimulates the respiratory musculature to work actively at specific intervals. Weakening of the respiratory muscles is reduced. This immediately shortens treatment duration times and weaning times, especially for patients receiving controlled respiratory assistance for a long period of time (e.g. several weeks). The respiratory musculature is exercised, enabling the patient to resume adequate spontaneous breathing more rapidly and be disconnected from the ventilator sooner. In cases in which the patient's incentive to breathe is suppressed by artificial means, the patient can more easily restart spontaneous breathing.

The stimulation apparatus can indirectly activate the respiratory musculature via stimulation of the nervous system connected to the respiratory musculature or directly through stimulation of the respiratory musculature itself. A combination of the two is also feasible.

Stimulation by the stimulation apparatus can be provided, instead of breathing assistance with a ventilator at a predefined interval. Stimulation is then appropriately performed at intervals between a specific number of breathing cycles. The number of breathing cycles depends on the patient's condition, the type of breathing support etc.

Stimulation by the stimulation apparatus can also be supplied in synchrony with the breathing assistance provided by the ventilator at the predefined interval. As used herein, "in synchrony" means that the course of events imitates a spontaneous breathing cycle, i.e. stimulation by the stimulation apparatus is provided so the ventilator supplies breathing assistance every time the respiratory musculature actively responds to a stimulation. A common control unit can then control both the ventilator and the stimulation apparatus.

As an alternative, the ventilator can respond with supporting respiratory assistance upon detection of a gas flow toward the lungs of the patient (normally referred to as triggering).

Simultaneous stimulation can be performed in each breathing cycle, thereby achieving the most natural breathing cycle, or at intervals between a number of breathing cycles. The number of breathing cycles can then be fixed or determined in conjunction with each stimulation delivered by the stimulation apparatus. In the latter instance, variation in the number of breathing cycles can be related to different patient parameters measured by a measurement unit. These patient parameters reflect the patient's condition, and the control unit can determine, on the basis thereof, whether shorter or longer intervals are needed between stimulations.

The following example illustrates the suitability of varying the interval. A patient, whose breathing is initially completely controlled by the ventilator, receives stimulation at e.g. three-breath intervals in order to prevent weakening of her/his respiratory musculature. The patient then attempts to breathe spontaneously as her/his condition improves. Since the patient then activates her/his own respiratory musculature, stimulation can be reduced to e.g. one every fifth breathing cycle. Additional improvements in the patient's spontaneous breathing further reduces the need for stimulation which can be reduced to e.g. once every tenth breathing cycle.

The reverse strategy may be more appropriate in other instances, i.e. a successive increase in the rate of stimulation. In controlled respiration, stimulation can be provided every tenth or twentieth breathing cycle in order to reduce weakening of the respiratory musculature. Stimulation could then be increased to occur every fifth or tenth breathing cycle to exercise the patient's respiratory musculature and encourage the patient to begin breathing on her/his own. Finally, stimulation can be provided after every or every other breathing cycle until the patient shows signs of being able to manage adequate spontaneous breathing without assistance.

There are also other possibilities. Utilization of stimulation of the respiratory musculature in respiratory therapy using a ventilator mainly depends on the patient's prerequisites and the type of treatment to be given.

Another possibility is e.g. to synchronize stimulation (and breathing support by the ventilator) with the patient's own attempts to breathe. This can be achieved by sensing the patient's nervous system, e.g. the phrenic nerve, in order to determine when the patient tries to breathe.

DESCRIPTION OF THE PREFERRED EMBODIMENTS

Figure 1:
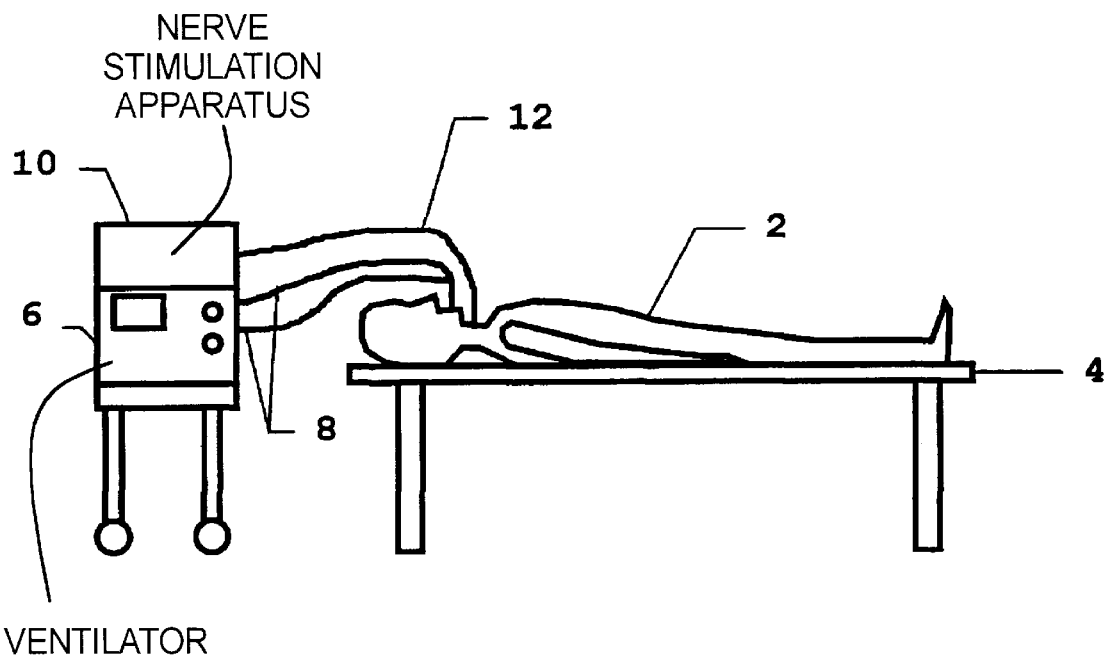
FIG. 1 shows a first embodiment of the system for assisted breathing according to the invention.
Figure 2:
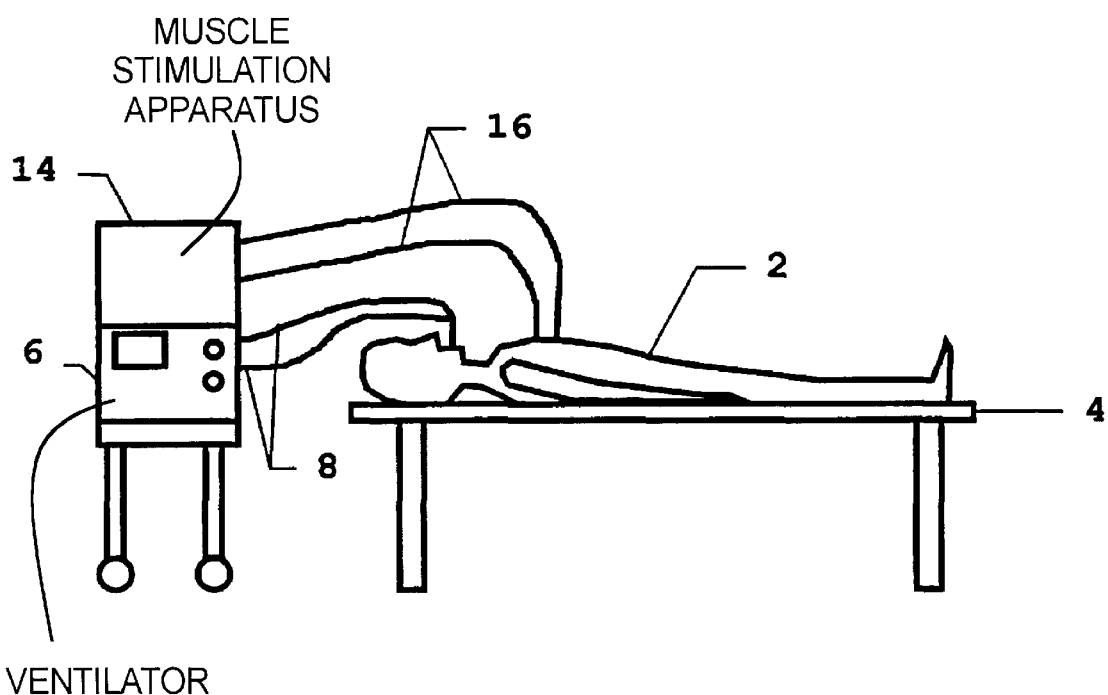
FIG. 2 shows a second embodiment of the system for assisted breathing according to the invention.
Figure 3:
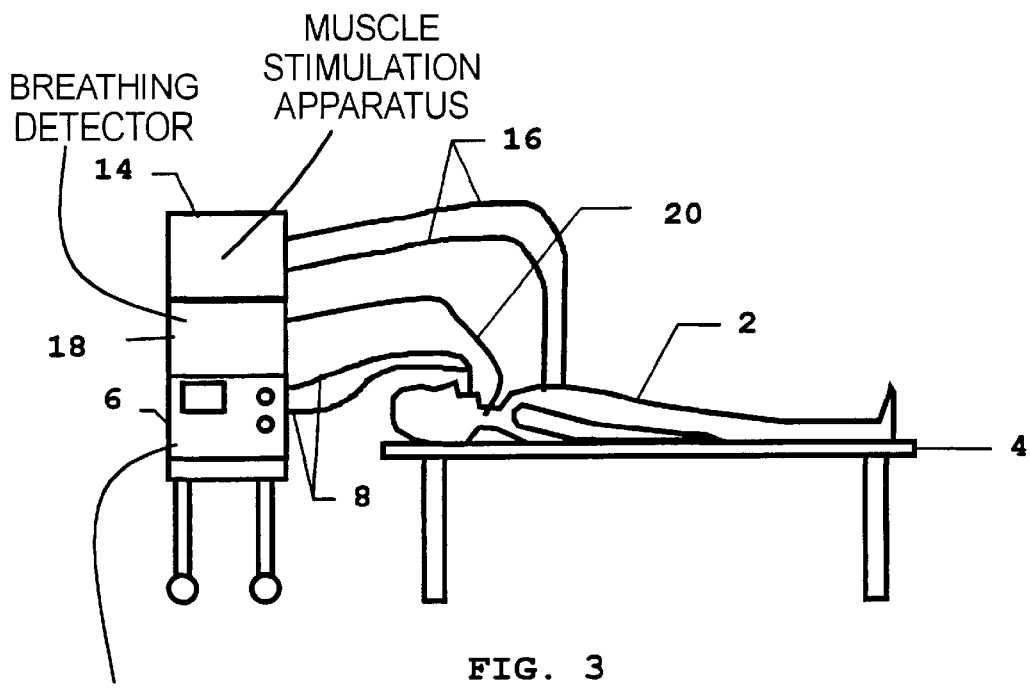
FIG. 3 shows a third embodiment of the system for assisted breathing according to the invention.

FIGS. 1–3 show three different embodiments of the system for assisted breathing, according to the invention, connected to a patient 2 on a bed 4. A ventilator 6 is connected to the patient 2 via a tubing system 8 for delivering breathing gas to the patient 2 according to the respiratory therapy selected by a doctor.

The respiratory therapy can consist of supportive treatment, in which the patient 2 retains some ability to breathe spontaneously, or controlled treatment, in which the ventilator 6 completely controls the respiration of the patient 2.

In the first embodiment (FIG. 1), a nerve stimulation apparatus 10 is connected, via a stimulation line 12, to the respiratory nerve system of the patient 2, e.g. to the phrenic nerve. The nerve stimulation apparatus 10 delivers stimulation pulses to the nerve. These stimulation signals are transferred to the musculature (primarily the diaphragm when the phrenic nerve is stimulated) and activates the same.

The nerve stimulation apparatus 10 and the ventilator 6 are interconnected to enable them to operate in synchrony. A large number of possible operating modes are then available.

Nerve stimulation can take place in every respiratory cycle, in synchrony with the breathing support provided by the ventilator 6.

The respiration assistance will then approach the most natural breathing mechanics. The ventilator 6 can in this case be set in a supportive mode, where breathing assistance is supplied upon detection of an inspiration (caused by the nerve stimulation)

In the alternative, the nerve stimulation can be fairly weak, so that the breathing muscles of the patient 2 do not become as highly activated as when the patient 2 takes a normal breath. However, activation of the muscles should be strong enough to keep them from becoming weakened during treatment. In such case, the two machines should be controlled together in an appropriate manner so that the stimulations are synchronized (especially during controlled breathing, when the ventilator 6 controls the breathing of the patient 2).

As used herein, "synchronous stimulation" refers to stimulation in physiological synchrony with breathing. In principle, a normal, spontaneous breath commences in the respiratory center in the medulla oblongata when various input signals from receptors in the body indicate that a breath should be taken. The respiratory center than generates breathing signals, which are carried by the nervous system to the respiratory musculature. Negative pressure develops in the lungs when the respiratory musculature is activated, and air is drawn into the lungs.

Analogous to this process, the nerve stimulation apparatus 10 emits stimulation signals at a time before the ventilator 6 starts delivering breathing gas to the patient 2. In principle, this time corresponds to the time it takes for the signal to reach the musculature and activate it.

Nerve stimulation also can be performed at specific intervals. Nerve stimulation then can be in synchrony with the breathing assistance provided by the ventilator 6 or in lieu of assistance by the ventilator 6. In the latter instance, stimulations must be strong enough to trigger adequate breaths. The ventilator 6 then only delivers breathing gas in the same way as to a patient 2 capable of spontaneous breathing.

These intervals can be fixed throughout the treatment or vary, depending on e.g. the condition of the patient 2. The latter will be described below in greater detail with regard to FIG. 4.

One or more stimulations can be emitted at the specific interval, e.g. three consecutive stimulations after every $20^{th}$ breathing cycle. The choice of interval, stimulation strength and the number of stimulations are wholly dictated by the prevailing situation and the patient 2. In principle, however, one of the purposes to deliver the stimulations is to prevent or reduce the weakening of the respiratory musculature normally occurring in a patient 2 whose respiration is controlled by a ventilator 6. Another purpose is to strengthen the respiratory musculature in initial attempts by the patient 2 to breathe spontaneously, all for the purpose of speeding up the patient's 2 weaning off the ventilator 6. A third purpose, of course, is to imitate a more natural way of breathing.

FIGS. 2 and 3 show an alternative way to activate the respiratory musculature. FIG. 2 accordingly depicts a second embodiment in which a muscle stimulation apparatus 14 is connected to the patient 2 via stimulation lines 16 for direct stimulation of the respiratory musculature. FIG. 2 only shows external electrodes connected to the patient 2, but muscle stimulation electrodes inside the patient, e.g. in the oesophagus, also can be used.

A third embodiment is shown in FIG. 3. This embodiment also incorporates a breathing detector 18, which senses the intrinsic nerve impulses of the patient 2 with a sensing line 20, in addition to the muscle stimulation apparatus. The sensing line 20 can be connected e.g. to the phrenic nerve.

The breathing signals, originating from the respiratory center of the patient 2, can be picked up by the breathing detector 18. stimulation of the respiratory musculature by the muscle stimulation apparatus 14 and/or breathing assistance by the ventilator 6 can then be synchronized with attempts at breathing/breathing made by the patient 2. This could be very beneficial to a patient 2 with injuries to or blockages in her/his nerve conduction system between the respiratory center and the respiratory musculature.

Figure 4:
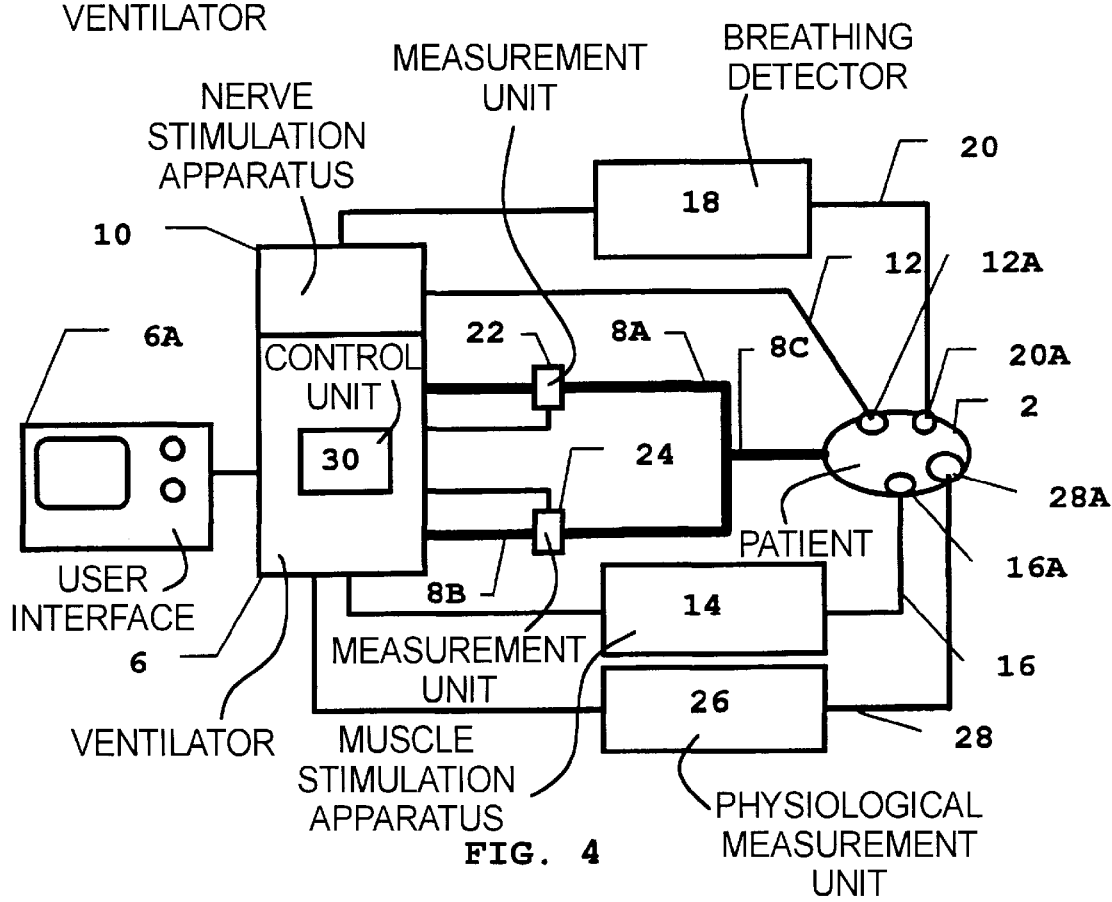
FIG. 4 shows a fourth embodiment of the system for assisted breathing according to the invention.

FIG. 4 shows a fourth embodiment in which the same designations are used for apparatuses and components identical to those in previous embodiments.

Thus, a ventilator 6 is connected to a (symbolically depicted) patient 2 via a tubing system 8. The tubing system includes an inspiratory tube 8A, an expiratory tube 8B and a patient connector 8G (e.g. a tracheal tube, face mask or similar). By means of a user interface 6A, a physician can program a complete treatment sequence for the patient 2. Information on the treatment's progress, measurement values and programmed values and setting can be shown on a display or monitor.

A nerve stimulation apparatus 10 is connected to the patient 2 via a stimulation line 12 and stimulation electrode 12A for stimulating the patient's respiratory nerve system, e.g. the phrenic nerve.

A breathing detector 18 is connected to the patient 2 via a sensing line 20 and the sensing electrode 20A in order to sense signals generated in the respiratory center of the patient 2. These signals are sent to the nerve stimulation apparatus 10 and ventilator 6.

A muscle stimulation apparatus 14 is connected to the respiratory musculature of the patient 2 via a stimulation line 16 and stimulation electrode 16A.

A flow meter, pressure gauge and possibly a gas meter, are arranged in a first measurement unit 22, installed inside the inspiratory tube 8A (possibly inside the ventilator 6), and in a second measurement unit 24, installed inside the expiratory tube 8B (possibly inside the ventilator 6). A number of gas-related parameters can be determined for the patient from measurement values supplied by the measurement units 22, 24.

A physiological measurement unit 26 is connected to the patient 2 via a measurement line 28 and a measurement body 28A. Physiological parameters, such as blood pressure, blood values, body temperature etc., can be determined with the physiological measurement unit 26. The physiological measurement unit 26 is connected to the ventilator 6.

The ventilator 6 includes s a control unit 30. The control unit 30 collects all information relevant to treatment of the patient 2, i.e. programmed data from the user interface 6A, measurement signals from the first and second measurement units 22, 24 of the breathing detector 18 and information from the physiological measurement unit 26. The treatment programmed by the physician can then be optimized on the basis of acquired information.

When the patient 2 generates adequate breathing signals in her/his respiratory center, synchronization with these signals can be performed via the ventilator 6. Any necessary amplification of the nerve signals is performed by the nerve stimulation apparatus 10. Additional assistance can also be provided via the muscle stimulation apparatus 14.

Since the condition of the patient 2 is monitored so accurately by the apparatus in the system for assisted breathing, treatment can be varied according to that condition.

If e.g. the patient's breathing capability for some reason is completely compromised, combined stimulation at specific intervals can be performed as described above. Weakening of the musculature can then be reduced by stimulation with the nerve stimulation apparatus 10 and/or the muscle stimulation apparatus 14. For example, stimulation can be performed every $20^{th}$ breathing cycle.

When the condition of the patient 2 improves and she/he makes sporadic attempts to breathe naturally, adaptation to these attempts can be made in combination with intensified muscle stimulation, e.g. stimulation every $10^{th}$ breathing cycle. This would increase exercise of the musculature and prepare the patient 2 for the time when the patient 2 starts taking over an increasing part of the breathing.

When the condition of the patient 2 further improves, with an increased degree of intrinsic respiratory activity, stimulation can be performed at varying intervals related to the patient's intrinsic activity.

For example, direct or indirect stimulation of the musculature can be provided when the patient 2 is not breathing on her/his own, thereby maintaining and increasing the strength of her/his respiratory musculature.

Alternately, stimulation can be performed when the patient 2 is able to breathe on her/his own in order to strengthen activation of her/his musculature.

A combination, in which stimulation is performed at the same time as virtually every breath, is also fully feasible.

A consequence of maintaining and possibly exercising the respiratory musculature of the patient 2 is that the dependence of the patient 2 on the ventilator 6 ends sooner. This means that the duration of hospital treatment can be greatly reduced. Being able to return home sooner will make the patient 2 feel better, and the risk of sequel diseases will also be reduced when treatment times are shorter.

Moreover, It will be possible to treat more patients at hospitals when treatment durations are reduced. This would benefit other sick or injured people and society as a whole.

Combinations of treatment procedures other than those described above are also possible. The basic feature of the invention is a system for assisted breathing employing a ventilator (respirator, anaesthesia machine or some other breathing apparatus) in combination with an apparatus for stimulating the respiratory musculature (nerve stimulation or muscle stimulation).

Although modifications and changes may be suggested by those skilled in the art, it is the intention of the inventors to embody within the patent warranted hereon all changes and modifications as reasonably and properly come within the scope of their contribution to the art.

We claim as our invention:

1. A system comprising:
    a ventilator adapted for connection to a living subject for delivering a breathing gas to said subject to assist breathing by said subject respectively at specified gas delivery intervals; and
    a stimulation apparatus adapted for connection to said subject for stimulating at least one of anatomical systems of said subject which participate in breathing, selected from the group consisting of the respiratory nervous system and the respiratory musculature, said stimulation apparatus emitting a stimulation signal to artificially stimulate a breath by said subject at specified intervals respectively preceding said gas delivery intervals.

2. A system as claimed in claim 1 wherein said stimulation apparatus emits said stimulation signal at a specified interval comprising a predetermined number of breathing cycles of said subject.

3. A system as claimed in claim 1 wherein said stimulation apparatus emits said stimulation signal to replace delivery of said breathing gas by said ventilator at said specified intervals.

4. A system as claimed in claim 1 wherein said specified intervals each comprise one breathing cycle.

5. A system as claimed in claim 1 wherein said specified intervals each comprise a fixed number of breathing cycles.

6. A system as claimed in claim 1 wherein said specified intervals each consist of a variable number of breathing cycles, and said system further comprising a control unit connected to said stimulation apparatus for selecting a number of breathing cycles comprising each of said specific intervals.

7. A system as claimed in claim 6 further comprising a measurement system adapted for connection to said patient for identifying a physiological patient parameter, said measurement system supplying a signal representing said parameter to said control unit, and said control unit comprising means for selecting said number of breathing cycles dependent on said parameter.

8. A system as claimed in claim 1 further comprising a breathing detector adapted for connection to the nervous system of said subject to sense signals generated in a respiratory center of said nervous system, and said stimulation apparatus emitting said stimulation signal upon detection of an attempt to breath by said subject sensed by said breathing detector.

9. A method for assisting breathing of a subject, comprising the steps:

connecting a subject to a ventilator and delivering breathing gas to said subject from said ventilator to assist breathing by said subject at respective gas delivery intervals; and connecting said subject to a stimulation apparatus and stimulating an anatomical portion of said subject which participates in breathing, selected from the group consisting of the respiratory nervous system and the respiratory musculature, and emitting said stimulation signal at respective specified intervals respectively preceding said gas delivery intervals.

10. A method as claimed in claim 9 wherein the step of emitting said stimulation signal at specified intervals comprises emitting said stimulation signal at a predetermined number of breathing cycles by said subject.

11. A method as claimed in claim 9 comprising emitting said stimulation signal to stimulate breathing as a replacement for delivery of said breathing gas to said subject by said ventilator.

12. A method as claimed in claim 9 comprising the additional step of synchronizing delivery of said breathing gas by said ventilator with said specific intervals at which said stimulation signal is emitted.

13. A method as claimed in claim 9 comprising emitting said stimulation signal at specified intervals each comprising one breathing cycle by said subject.

14. A method as claimed in claim 9 comprising emitting said stimulation signal at specified intervals each comprising a fixed number of breathing cycles by said subject.

15. A method as claimed in claim 9 comprising emitting said stimulation signal at specified intervals which are variable, and varying said specified intervals to comprise a selected number of breathing cycles.

16. A method as claimed in claim 15 comprising measuring a physiological parameter of said subject, and selecting said number of breathing cycles dependent on said parameter.

17. A method as claimed in claim 9 comprising monitoring the nervous system of said subject to sense signals generated in a respiratory center of said subject, and emitting said stimulation signal at specified intervals dependent on attempts to breath by said subject identified by said sensed signals from said respiratory center.

\* \* \* \* \*